US 011328508B2

(12) United States Patent
Wright et al.

(10) Patent No.: US 11,328,508 B2
(45) Date of Patent: May 10, 2022

(54) ALERTS BASED ON CORNEAL REFLECTIONS

(71) Applicant: Nokia Technologies Oy, Espoo (FI)

(72) Inventors: Christopher Wright, London (GB); Matthew Lawrenson, Chesterfield, MO (US)

(73) Assignee: NOKIA TECHNOLOGIES OY, Espoo (FI)

( * ) Notice: Subject to any disclaimer, the term of this patent is extended or adjusted under 35 U.S.C. 154(b) by 0 days.

(21) Appl. No.: 17/030,224

(22) Filed: Sep. 23, 2020

(65) Prior Publication Data

US 2021/0103732 A1 Apr. 8, 2021

(30) Foreign Application Priority Data

Oct. 3, 2019 (EP) .................................... 19201352

(51) Int. Cl.
*G06V 20/20* (2022.01)
*G06T 7/70* (2017.01)
*G08B 21/18* (2006.01)
*G06V 40/19* (2022.01)

(52) U.S. Cl.
CPC ............... *G06V 20/20* (2022.01); *G06T 7/70* (2017.01); *G06V 40/19* (2022.01); *G08B 21/18* (2013.01)

(58) Field of Classification Search
CPC .................................... G06T 7/70; G08B 21/18
See application file for complete search history.

(56) References Cited

U.S. PATENT DOCUMENTS

| 9,846,307 | B2 | 12/2017 | Tremblay et al. |
| 2002/0101568 | A1* | 8/2002 | Eberl ................. G02B 27/0172 351/211 |
| 2016/0014332 | A1 | 1/2016 | de Leon et al. |
| 2016/0166140 | A1 | 6/2016 | Lawrenson et al. |
| 2016/0216837 | A1 | 7/2016 | Nolan et al. |
| 2017/0220106 | A1 | 8/2017 | Tomiyama et al. |
| 2017/0228128 | A1 | 8/2017 | Lawrenson et al. |
| 2017/0249450 | A1 | 8/2017 | Lawrenson et al. |
| 2017/0352128 | A1 | 12/2017 | Sasao et al. |

(Continued)

FOREIGN PATENT DOCUMENTS

| BR | 112017003963 A2 | 12/2017 |
| BR | 112017028279 A2 | 9/2018 |
| RU | 2672502 C1 | 11/2018 |

(Continued)

OTHER PUBLICATIONS

Nitschke et al., "Corneal Imaging Revisited: an Overview of Corneal Reflection Analysis and Applications", IPSJ Transactions on Computer Vision and Applications, vol. 5, 2013, pp. 1-18.

(Continued)

*Primary Examiner* — Edward Park
(74) *Attorney, Agent, or Firm* — Alston & Bird LLP

(57) ABSTRACT

According to various, but not necessarily all, embodiments there is provided an apparatus comprising means for: capturing at least one image of a cornea of the user; processing the at least one image to detect one or more objects and/or activities based on one or more reflections by a peripheral portion of the cornea; and providing an alert to the user for alerting the user to the detection of the one or more objects and/or activities.

20 Claims, 8 Drawing Sheets

(56) References Cited

U.S. PATENT DOCUMENTS

Figure 1A:
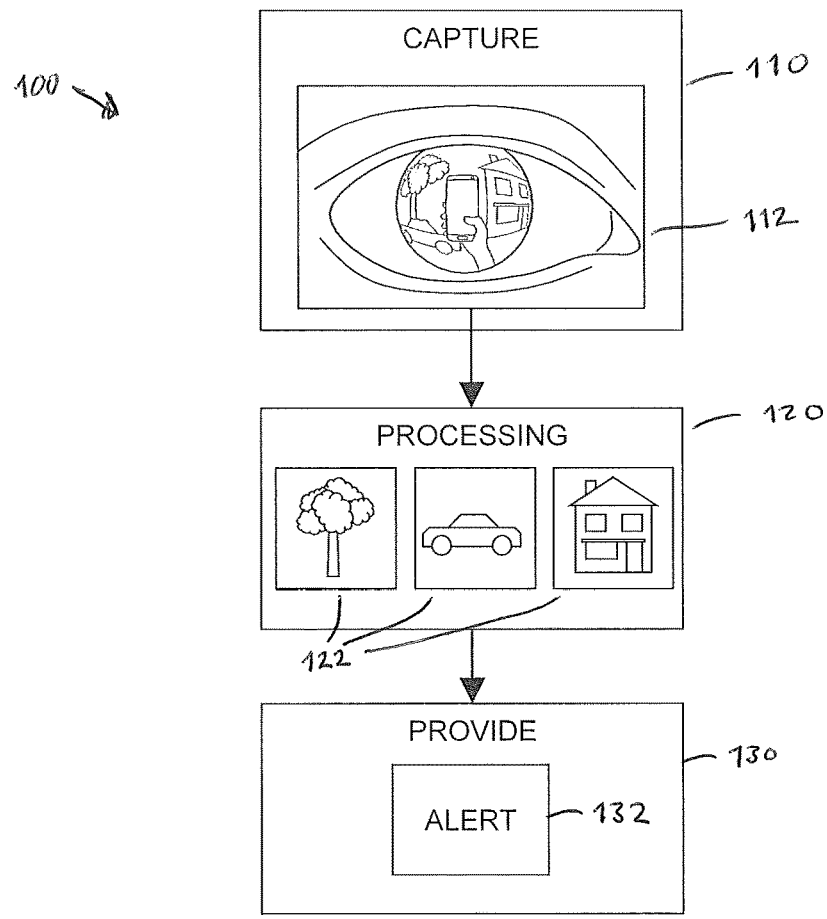

2019/0222817 A1* 7/2019 Abou Shousha ........ A61B 3/14

FOREIGN PATENT DOCUMENTS

| WO | 2016/036294 A1 | 3/2016 |
| WO | 2017/003330 A1 | 1/2017 |
| WO | 2018/008232 A1 | 1/2018 |

OTHER PUBLICATIONS

Plopski, "Improving Optical-seethrough Experience Through Corneal Imaging", Thesis, Jan. 2016, 148 pages.

"The Psychosocial Toll of Our Increasingly Online Lives", Science Blog, Retrieved on Sep. 23, 2020, Webpage available at: https://scienceblog.com/501347/the-psychosocial-toll-of-our-increasingly-online-lives/.

"Why Parents Really Need to Put Down Their Phones", Psychology Today, Retrieved on Sep. 23, 2020, Webpage available at: https://www.psychologytoday.com/us/blog/going-beyond-intelligence/201711/why-parents-really-need-put-down-their-phones.

"Foveal", Wikipedia, Retrieved on Sep. 23, 2020, Webpage available at: https://en.wikipedia.org/wiki/Foveal.

"Peripheral Vision", Wikipedia, Retrieved on Sep. 23, 2020, Webpage available at: https://en.wikipedia.org/wiki/Peripheral_vision.

"The World in an Eye", Cs.Columbia, Retrieved on Sep. 23, 2020, Webpage available at: https://www.cs.columbia.edu/CAVE/projects/world_eye/.

"Google's latest object recognition tech can spot everything in your living room", Engadget, Retrieved on Sep. 23, 2020, Webpage available at: https://www.engadget.com/2014-09-08-google-details-object-recognition-tech.html.

"Object Detection: An End to End Theoretical Perspective", Towards Data Science, Retrieved on Sep. 23, 2020, Webpage available at: https://towardsdatascience.com/object-detection-using-deep-learning-approaches-an-end-to-end-theoretical-perspective-4ca27eee8a9a.

Timmis et al., "The Impact of Mobile Phone Use on Where We Look and How We Walk When Negotiating Floor based Obstacles", Pios One, Jun. 30, 2017, pp. 1-20.

Lim et al., "Effects of Smartphone Texting on the Visual Perception and Dynamic Walking Stability", Journal of Exercise Rehabilitation, vol. 13, No. 1, 2017, pp. 48-54.

Nishino et al., "Corneal Imaging System: Environment from Eyes", International Journal on Computer Vision, vol. 70, No. 1, 2006, pp. 23-40.

Simonyan et al., "Two-Stream Convolutional Networks for Action Recognition in Videos", Advances in Neural Information Processing Systems, 2014, pp. 1-9.

Extended European Search Report received for corresponding European Patent Application No. 19201352.2, dated Mar. 24, 2020, 12 pages.

* cited by examiner

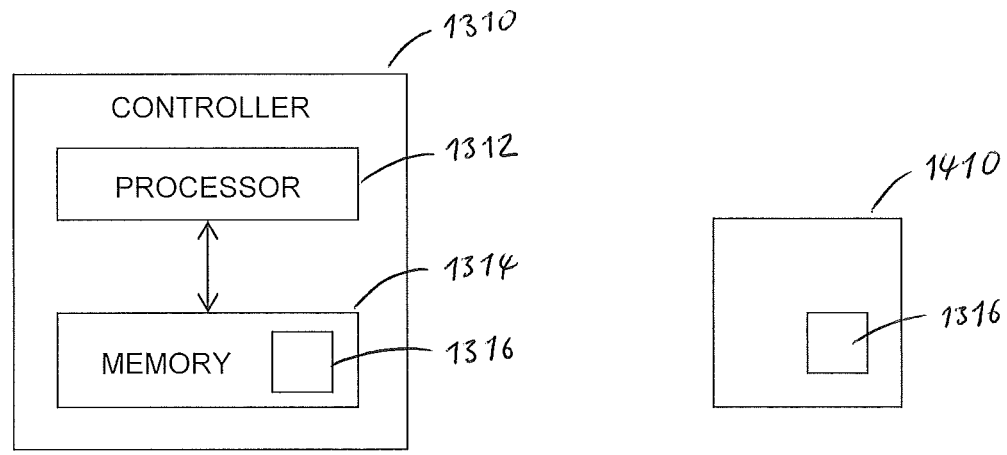
FIG. 13
FIG. 14
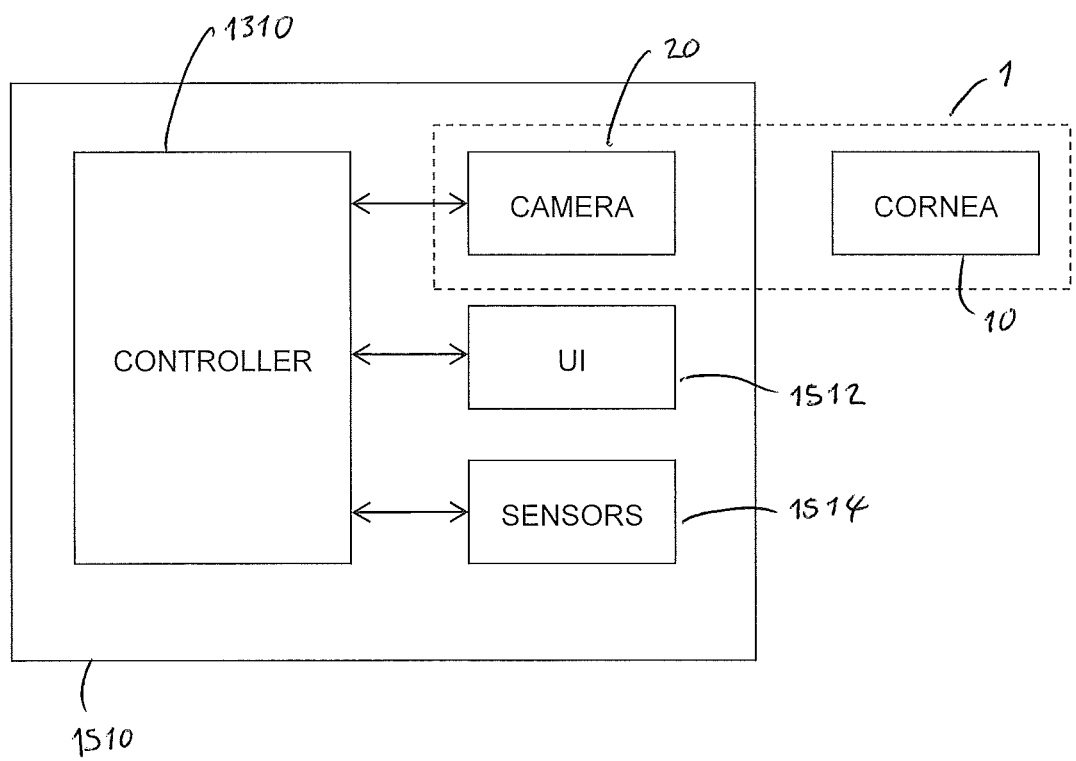
FIG. 15

ALERTS BASED ON CORNEAL REFLECTIONS

TECHNOLOGICAL FIELD

Embodiments of the present disclosure relate to alerts based on corneal reflections. Some relate to alerts to a detection of objects and/or activities detected based on corneal reflections.

BACKGROUND

Central vision has the highest visual acuity. Peripheral vision, by comparison, is weak for humans and has a reduced resolution of detail, color, and shape as compared to central vision. Peripheral vision nevertheless plays an important role in a person's situational awareness.

When a person's central vision is focused towards a task to which they are attending, there is an increased demand on their central vision and a reduction in their situation awareness.

BRIEF SUMMARY

According to various, but not necessarily all, embodiments there is provided an apparatus comprising means for: capturing at least one image of a cornea of the user; processing the at least one image to detect one or more objects and/or activities based on one or more reflections by a peripheral portion of the cornea; and providing an alert to the user for alerting the user to the detection of the one or more objects and/or activities.

According to various, but not necessarily all, embodiments there is provided a method comprising: capturing at least one image of a cornea of the user; processing the at least one image to detect one or more objects and/or activities based on one or more reflections by a peripheral portion of the cornea; and providing an alert to the user for alerting the user to the detection of the one or more objects and/or activities.

According to various, but not necessarily all, embodiments there is provided a computer program that, when run on a computer, performs: causing at least one image of a cornea of the user to be captured; processing the at least one image to detect one or more objects and/or activities based on one or more reflections by a peripheral portion of the cornea; and causing an alert to be provided to the user for alerting the user to the detection of the one or more objects and/or activities.

The following portion of this 'Brief Summary' section, describes various features that may be features of any of the embodiments described in the foregoing portion of the 'Brief Summary' section. The description of a function should additionally be considered to also disclose any means suitable for performing that function.

Detecting one or more objects and/or activities based on one or more reflections by a peripheral portion of the cornea may comprises: detecting one or more objects and/or activities based on one or more reflections by the cornea; determining which of the one or more objects and/or activities are represented in a portion of the at least one image corresponding to the peripheral portion of the cornea; and selecting those one or more objects and/or activities which are determined to be represented in the portion of the at least one image corresponding to a peripheral portion of the cornea.

A portion of the at least one image corresponding to a central portion of the cornea may be removed before processing the at least one image to detect one or more objects and/or activities based on one or more reflections by the peripheral portion of the cornea.

A perimeter of the cornea in the at least one image may be determined. The portions of the at least one image corresponding to central and peripheral portions of the cornea may be determined based on the perimeter. A radius of a boundary between the central and peripheral portions of the cornea may be a fixed percentage of the radius of the cornea.

An alert may be provided to the user for alerting the user to a detection of a first one or more objects and/or activities. No alert may be provided to the user for alerting the user to a detection of a second, different one or more objects and/or activities.

Objects and/or activities detected based on one or more reflections by a central portion of the cornea may be recorded. It may be determined whether the one or more objects and/or activities detected based on one or more reflections by the peripheral portion of the cornea correspond to an object and/or activity detected based on one or more reflections by the central portion of the cornea during a preceding period of time. In some examples, if the one or more objects and/or activities detected based on one or more reflections by the peripheral portion of the cornea correspond to an object and/or activity detected based on one or more reflections by the central portion of the cornea during the preceding period of time, no alert is provided to the user for alerting the user to the detection of the one or more objects and/or activities.

It may be determined whether the user is interacting with the one or more objects and, in some examples, if the user is determined to be interacting with the one or more objects, no alert is provided to the user for alerting the user to the detection of the one or more objects.

Determining whether the user is interacting with the one or more objects may comprise processing the at least one image to detect whether the user is in physical contact with the one or more objects.

At least one image of a left cornea of the user and at least one image of a right cornea of the user may be obtained.

A proximity of the one or more objects to the user may be determined based on a parallax of the one or more objects between the at least one image of a left cornea of the user and at least one image of a right cornea of the user.

In some examples, if the one or more objects are within a threshold proximity, no alert is provided to the user for alerting the user to the detection of the one or more objects.

The provision of the alert to the user for alerting the user to the detection of the one or more objects may be conditional on one or more properties of the one or more objects.

The one or more properties may comprise one or more of: an identity of the one or more objects; a location of the one or more objects relative to the user; a movement of the one or more objects.

A plurality of images of the cornea of the user may be captured at different times.

One or more activities can be determined based on changes concerning the one or more objects between the plurality of images.

In some examples, the provision of the alert to the user for alerting the user to the detection of the one or more objects and/or activities is conditional on an identity of the determined one or more activities.

The alert may comprise a visual output.

The capturing of and the processing of the at least one image may be at least substantially transparent to the user.

Visual content may be displayed while capturing and processing the at least one image.

The alert may comprise a temporary interrupt to the displayed visual content.

The temporary interrupt may comprise displaying a visual representation of the one or more objects and/or activities to the user.

The alert may comprise a haptic output and/or an auditory output.

The alert may be configured to indicate a location of the one or more objects and/or activities relative to the user.

The detection of the one or more objects and/or activities and the provision of the alert may occur in substantially real-time.

The provision of the alert may be conditional on a determination that the user is looking at the apparatus when the at least one image is captured.

Determining that the user is looking at the apparatus when the at least one image is captured may comprise processing the at least one image to detect whether the apparatus is reflected by the central portion of the cornea.

A transformation, based on a geometric model of the cornea, may be applied to the at least one image.

A point spread function may be determined based on a comparison of displayed visual content as reflected by the cornea of the user with the visual content as displayed. A deconvolution, based on the point spread function, of the at least one image may be performed.

Processing the at least one image of the cornea of the user to detect one or more objects and/or activities may comprise using computer vision to recognise the one or more objects and/or activities in the at least one image.

Audio data may be obtained and processed to detect sounds associated with the one or more objects and/or activities recognised using computer vision.

The at least one image of a cornea of the user may be captured using a camera disposed proximate a display and configured to receive light from a field of view in front of the display.

According to various, but not necessarily all, embodiments there is provided examples as claimed in the appended claims.

BRIEF DESCRIPTION

Figure 1B:
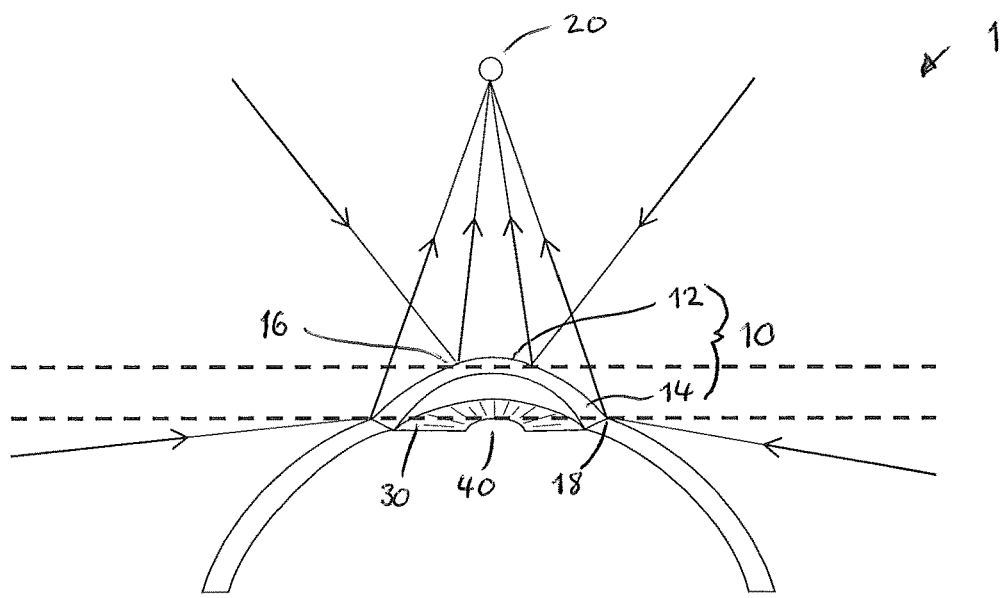
Figure 2:
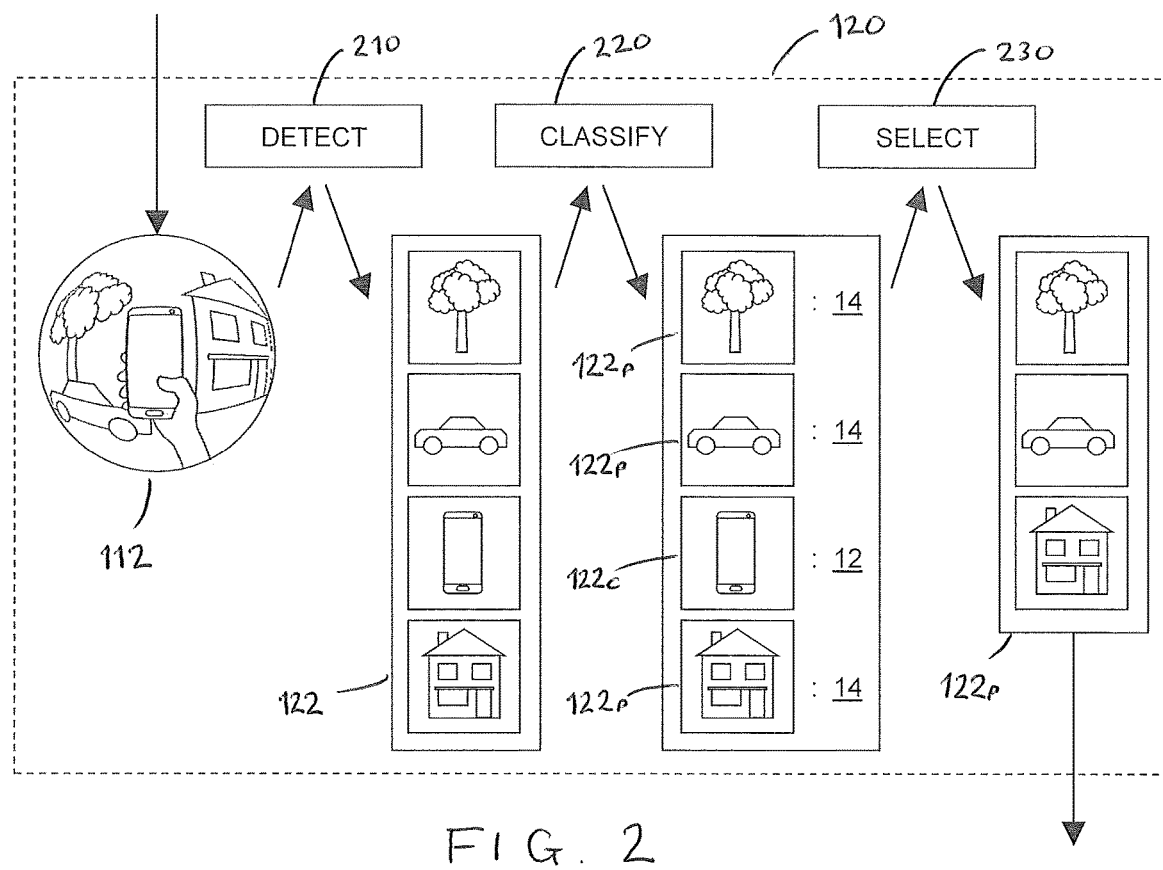
Figure 3:
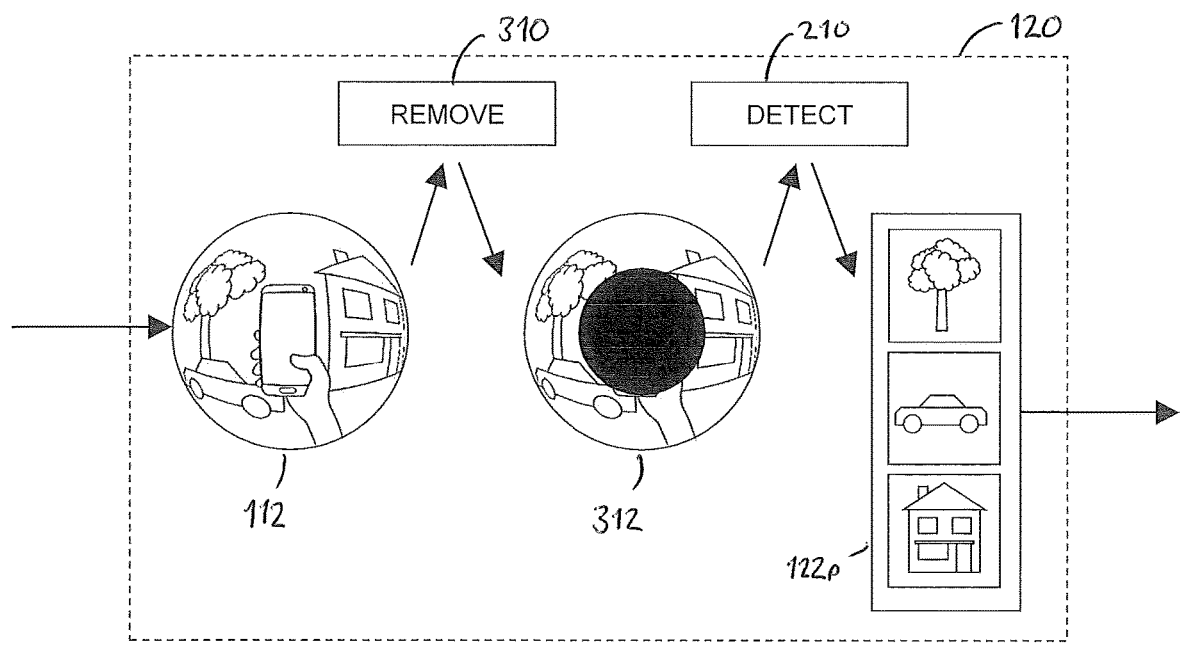
Figure 4A:
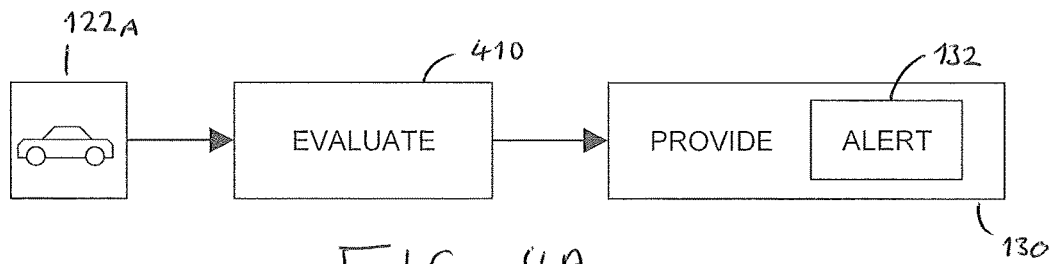
Figure 5:
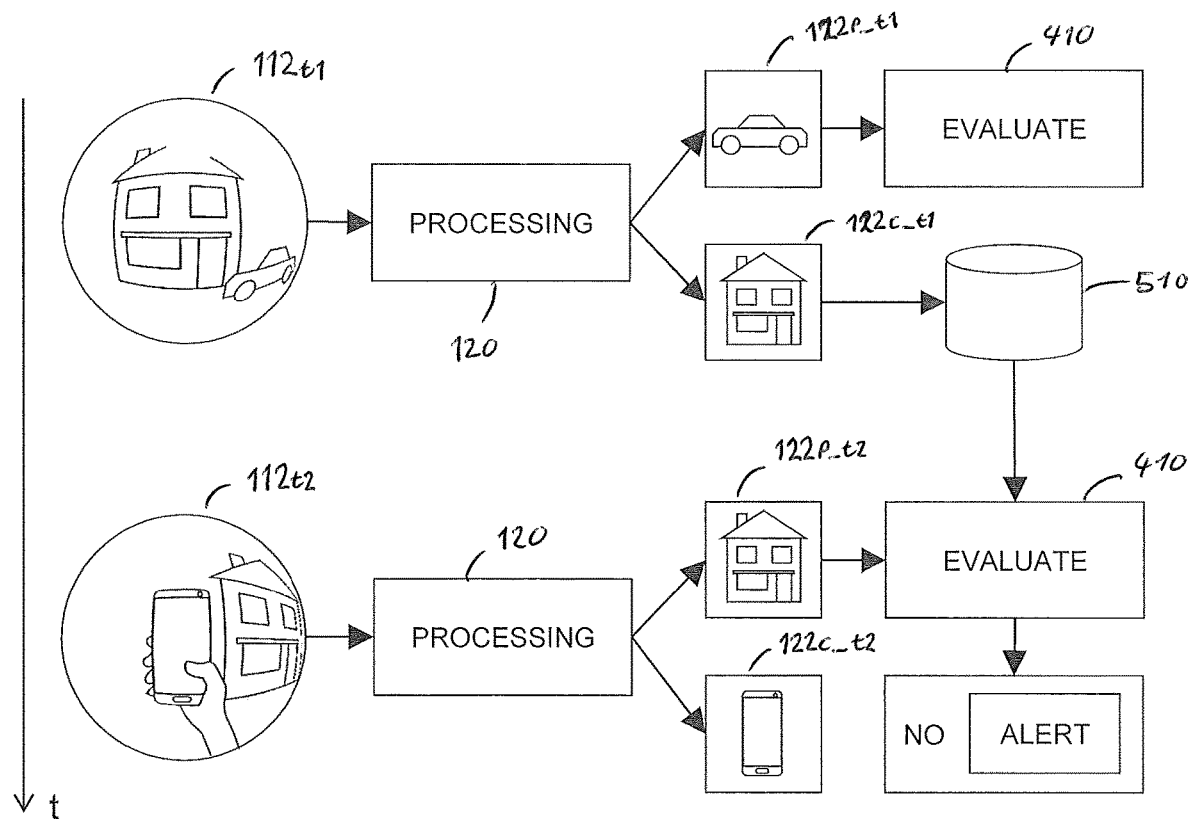
Figure 6:
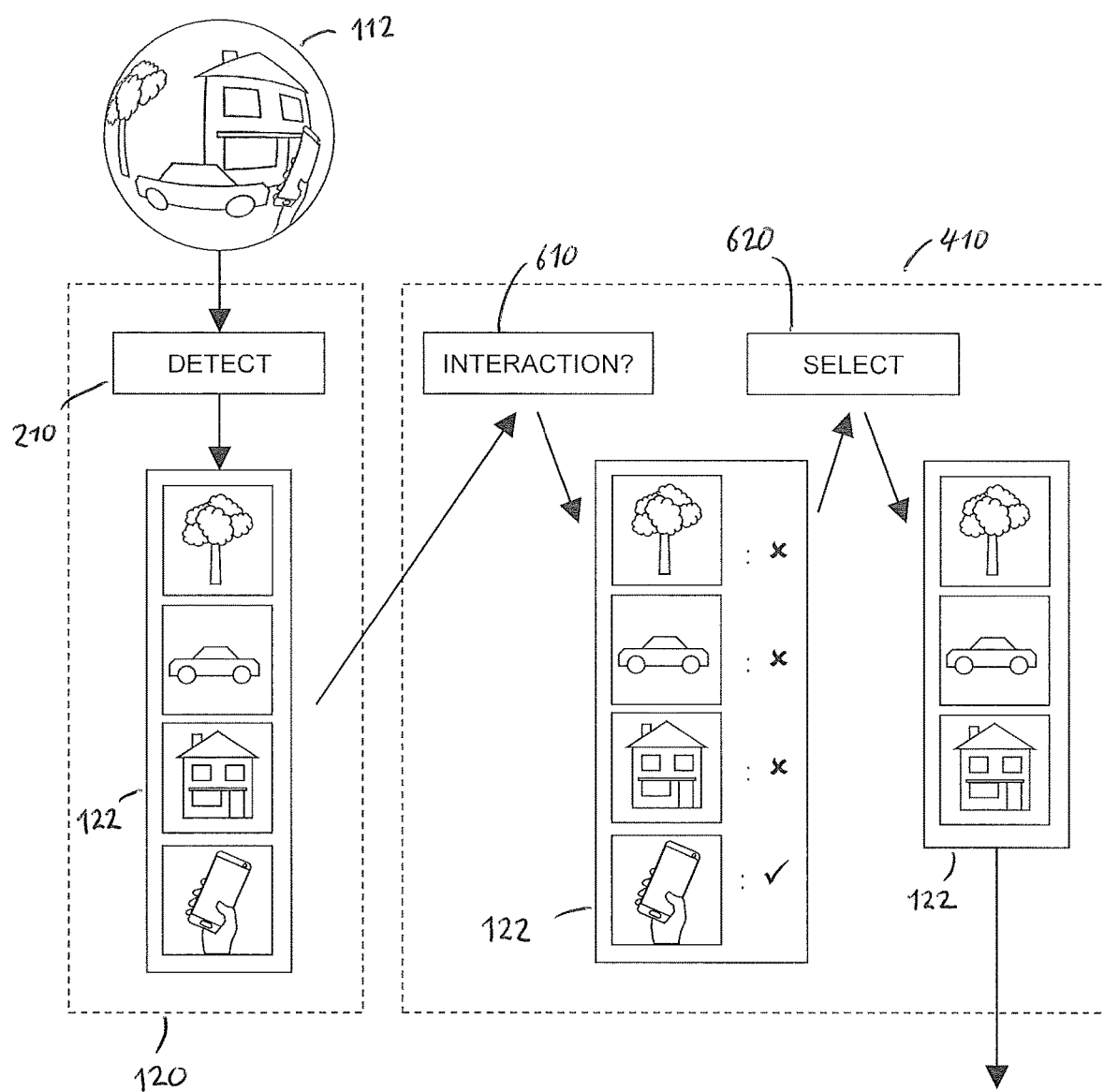
Figure 7:
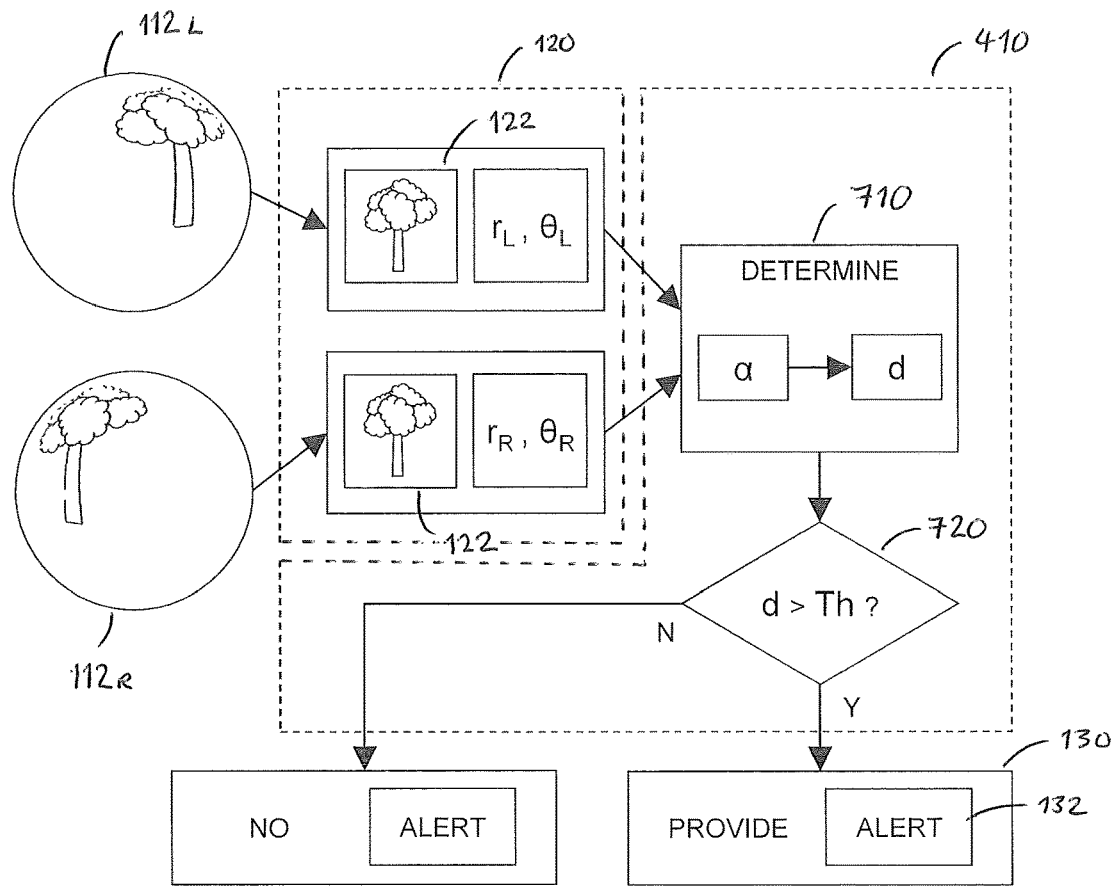
Figure 8:
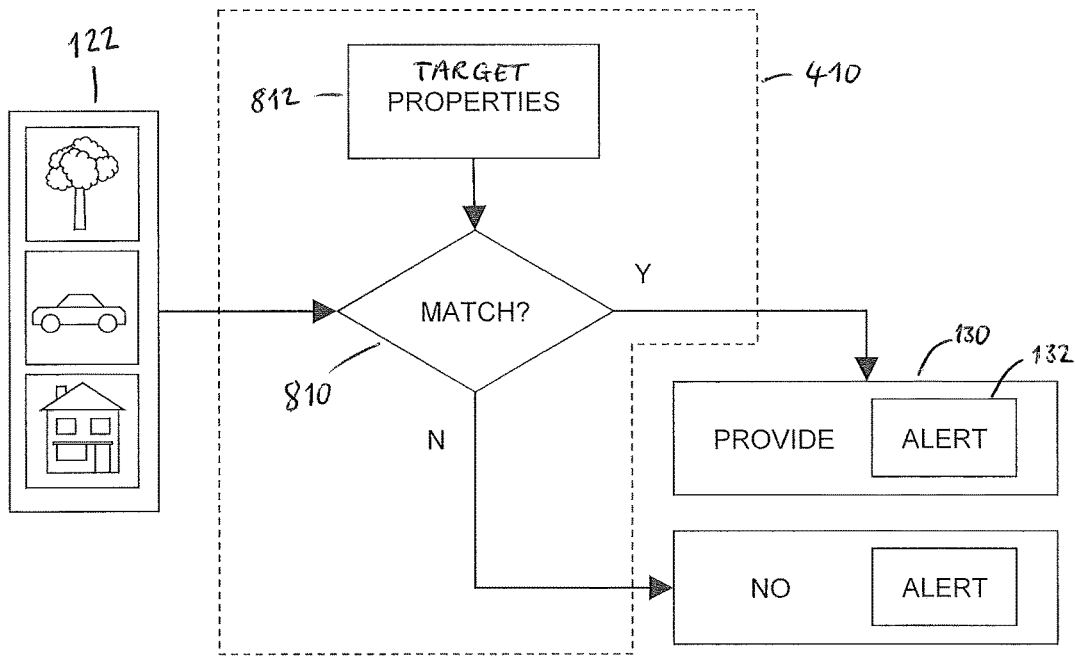
Figure 9:
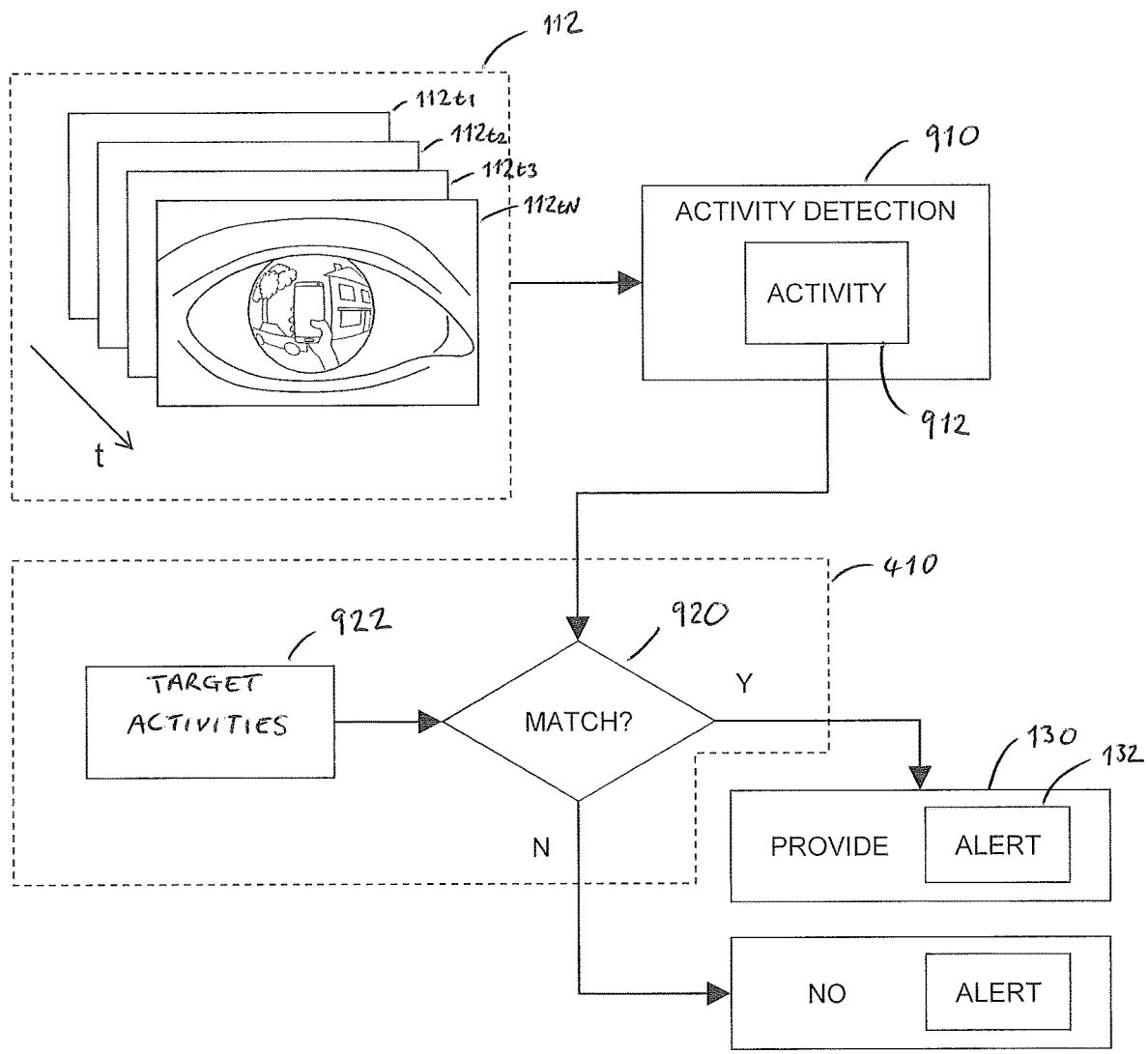
Figure 10:
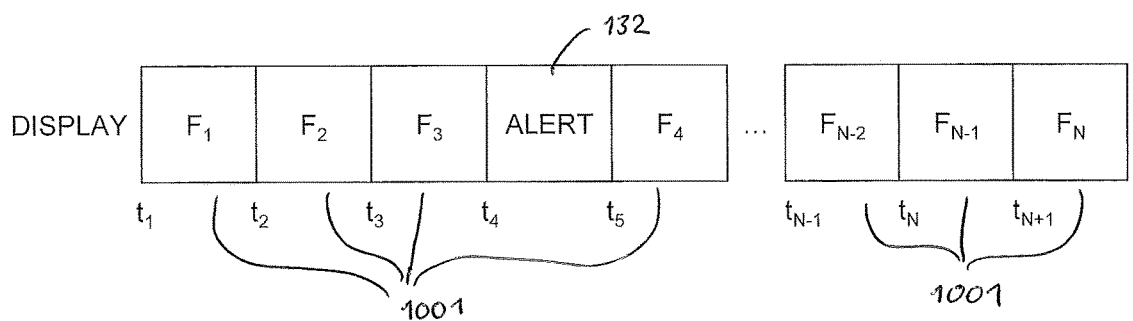
Figure 11:
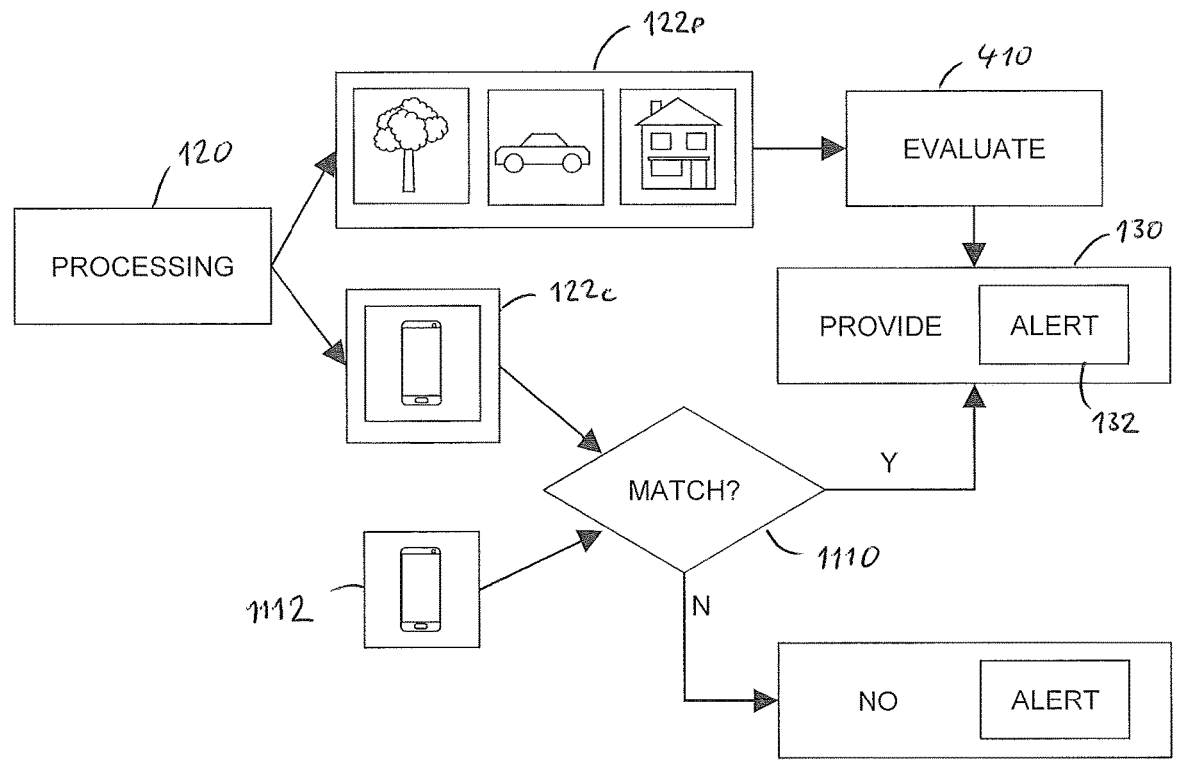
Figure 12:
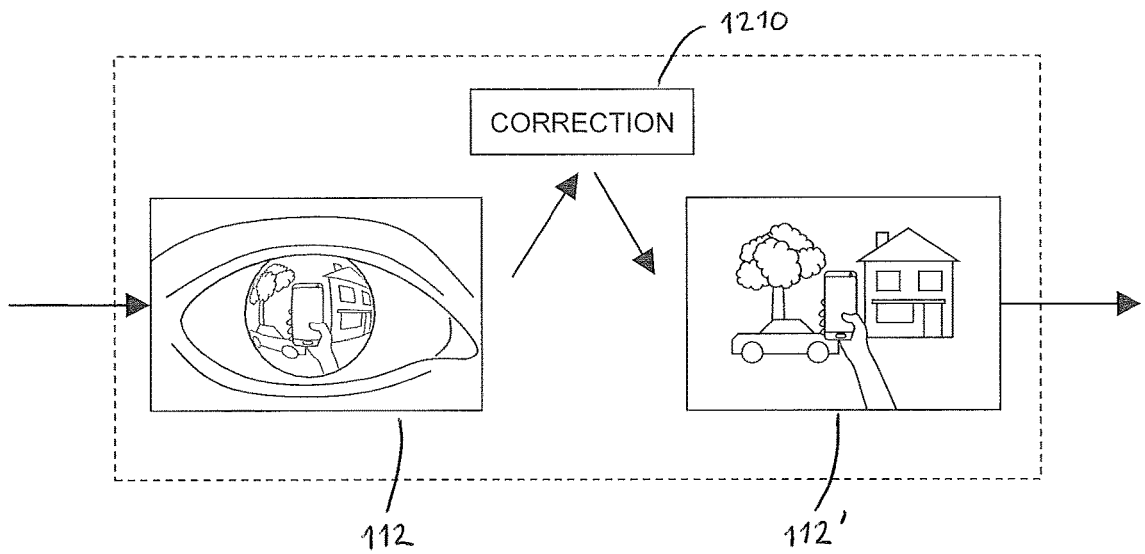

Some examples will now be described with reference to the accompanying drawings in which:

FIG. 1A shows an example of a method described herein;
FIG. 1B shows an example of a cornea;
FIG. 2 shows an example of a method as described herein;
FIG. 3 shows an example of a method as described herein;
FIGS. 4A and B show examples of a method as described herein;
FIG. 5 shows an example of a method as described herein;
FIG. 6 shows an example of a method as described herein;
FIG. 7 shows an example of a method as described herein;
FIG. 8 shows an example of a method as described herein;
FIG. 9 shows an example of a method as described herein;
FIG. 10 shows an example of an alert as described herein;
FIG. 11 shows an example of a method as described herein;
FIG. 12 shows an example of a method as described herein;
FIG. 13 shows an example of a controller as described herein;
FIG. 14 shows an example of a delivery mechanism as described herein; and FIG. 15 shows an example of an apparatus as described herein.

DETAILED DESCRIPTION

FIG. 1A illustrates an example of a method 100 for alerting a user to objects or activities 912 in their environment. The method 100 can improve a situational awareness of the user.

At block 110, the method 100 comprises capturing at least one image 112 of a cornea 10 of a user. The cornea 10 is illustrated in FIG. 1B along with the sclera 20, iris 30, and pupil 40 for context. The at least one image 112 can be captured while visual content 1001 (see FIG. 10) related to a task to which the user is attending is displayed by an apparatus for performing the method 100.

The cornea 10 has a very smooth external surface covered in a thin tear film which makes it behave as a mirror. As a result, the cornea 10 can, in combination with a camera 20 or other means suitable for capturing the at least one image 112, form a catadioptric system 1 (shown in FIG. 1B). Because of cornea 10 forms a convex mirror, a wide-angle field of view of the environment of the user can be obtained from the at least one image 112. For example, light from the user's far peripheral visual filed can be reflected into the camera 20 as shown in FIG. 1B. This wide-angle field of view may be much wider than the field of view of the camera 20 or of other cameras comprised in an apparatus for performing the method 100.

At block 120, the method 100 comprises processing the at least one image 112 to detect one or more objects 122 and/or activities 912 (shown in FIG. 9) based on reflections by a peripheral portion 14 of the cornea 10. This can comprise detection of one or more objects 122 reflected by the peripheral portion 14 of the cornea 10 in the at least one image 112 or can comprise detection of one or more activities 912 from processing a plurality of images 112 such as frames in a captured video.

The peripheral portion 14 of the cornea 10 is shown in FIG. 1B and is a portion of the cornea 10 which reflects light from at least a peripheral visual field of the user into the camera 20. It adjoins a central portion 12 of the cornea 10 at a boundary 16 and the sclera 20 at the limbus 18. The central portion 12 of the cornea 10 reflects light from at least a central visual field of the user into the camera 20. Light from the central visual field may fall on the macula whereas light from the peripheral visual field may fall on areas of the retina outside of the macula. The sclera 20 is not as highly reflective as the cornea 10.

Geometrically, the peripheral portion 14 comprises an ellipsoidal zone (surface of an ellipsoidal segment) of two bases. One base is defined by the plane in which the boundary 16 is comprised and the other base is defined by the plane in which the limbus 18 is comprised. The central portion 12 of the cornea 10 comprises an ellipsoidal zone of one base (surface of an ellipsoidal cap). This base is defined by the plane in which the boundary 16 is comprised.

In the at least one image 112 of the cornea 10, the peripheral portion 14 may be represented by a substantially annular region of the image 112 and the central portion 10 may be represented by a disc within this annular region of the image 112.

Processing the at least one image 112 of the cornea 10 of the user to detect one or more objects 122 and/or activities 912 can comprise the use of computer vision to recognise the one or more objects 122 and/or activities 912 in the at least one image 122 and, optionally, to return a position of representations of the one or more objects 122 and/or activities 912 within the at least one image 112. Processing the at least one image 112 of the cornea 10 of the user to detect one or more objects 122 and/or activities 912 based on one or more reflections by the peripheral portion 14 of the cornea 10 can comprise the use of computer vision to recognise the one or more objects 122 and/or activities 912 in the aforementioned substantially annular region of the image 112. Data from one or more further sensors 1514 (see FIG. 15) can, in some examples, be used to corroborate the recognition of objects and/or activities from image data.

At block 130, the method 100 comprises providing an alert 132 to the user for alerting the user to the detection of the one or more objects 122 and/or activities 912.

The alert 132 is a human-perceptible output which is configured to capture the attention of a user of an apparatus for performing the method 100. The output may be a visual output, an audio output, a haptic output, or any other output suitable for capturing the attention of the user.

The alert 132 is task-irrelevant with respect to a task to which the user is attending by interacting with an apparatus for performing the method 100. For example, the alert 132 is not called by the program instructions controlling a task to which the user is attending. The alert 132 may discriminably differ from other ongoing human-perceptible outputs of an apparatus for performing the method 100 such as displayed visual content related to a task to which the user is attending.

The alert 132 may prompt the user to take action. The nature of the action to be taken need not be communicated to the user by the alert 132. The nature of the action may not even be determined by the method 100 or apparatus for performing the method 100. Instead the nature of the action to be taken may be determined by the user, the alert 132 being merely a prompt to take action of any kind.

The method 100 can occur in substantially real-time. The detection of the one or more objects 122 and/or activities 912 and the provision of the alert 132 can occur in substantially real-time. As a result, the real-time situational awareness of the user can be improved.

Improving the situational awareness of the user can be an effective safety measure. For example, when a user is attending to a task, the user's perception of collision hazards can be reduced. Alerting the user to the detection of objects 122 and/or activities 912 in their environment improves their perception of said collision hazards. Thus, the user can take evasive action which they would not have otherwise been aware was required.

At a first level, the user is presumed to be aware of objects and/or activities within their central vision. Thus, the method 100 is directed to detecting and alerting the user to objects and/or activities falling outside of their central vision. FIGS. 2 and 3 illustrate examples of how the processing of block 120 of the method 100 detects, specifically, objects and/or activities based on reflections by the peripheral portion 14 of the cornea 10.

At another level, the user is presumed to be aware of some objects and/or activities which are not, at the time of capturing the at least one image 112, within their central vision. FIGS. 4A and 4B, 5, 6, and 7 illustrate examples of evaluating objects and/or activities falling outside of the user's central vision to determine whether the user is otherwise aware of them.

In the example of FIG. 2, one or more objects 122 reflected by the cornea are detected and afterwards a distinction is made between objects $122C$ reflected by the central portion 12 of the cornea 10 and objects $122_P$ reflected by the peripheral portion 14 of the cornea 10.

At block 210, the method 100, in this example, comprises detecting one or more objects 122 reflected by the cornea 10.

At block 220, the method 100, in this example, comprises determining which of the one or more objects 122 are represented in a portion of the at least one image 112 corresponding to the peripheral portion 14 of the cornea 10.

The determination effectively classifies the one or more objects 122 into one or more objects $122c$ reflected by the central portion 12 of the cornea 10 and one or more objects $122p$ reflected by the peripheral portion 14 of the cornea 10.

At block 230, the method 100, in this example, comprises selecting those one or more objects $122p$ which are determined to be represented in the portion of the at least one image 112 corresponding to a peripheral portion 14 of the cornea 10. These are then fed forward as an output from block 120 of the method 100.

Method blocks 210 to 230 can likewise be applied to make a distinction between reflections by the central portion 12 and by the peripheral portion 14 of the cornea 10 of the user. Based on this distinction, a further distinction can be made as between activities 912 which are detected based on one or more reflections by the central portion 12 and activities 912 which are detected based on one or more reflections by the peripheral portion 14.

In contrast to the example of FIG. 2, the example of FIG. 3 may not comprise the detection of objects $122c$ reflected by the central portion 12 of the cornea 10.

At block 310, the method 100, in this example, comprises removing a portion of the at least one image 112 corresponding to a central portion 12 of the cornea 10, resulting in a modified at least one image 312.

At block 210, the method 100, in this example, comprises processing the modified at least one image 312 to detect the one or more objects $122P$ reflected by the peripheral portion 14 of the cornea 10 and/or (though not illustrated) to detect one or more activities 912 based on one or more reflections by the peripheral portion 14. These are then fed forward as an output from block 120 of the method 100.

In the examples of both FIG. 2 and FIG. 3 the portions of the at least one image 112 which correspond respectively to the central portion 12 of the cornea 10 and the peripheral portion 14 of the cornea 10 can be determined based on a perimeter of the cornea 10 in the at least one image 112. The perimeter of the cornea 10 is the limbus 18. Methods for locating the limbus 18 in the at least one image 112 are described in Nishino, K., & Nayar, S. K. (2006). Corneal imaging system: Environment from eyes. *International Journal of Computer Vision,* 70(1), 23-40, in particular in section 3.1. "Limbus Localization" of the same. A radius of the boundary 16 between the central and peripheral portions 12, 14 of the cornea 10 can be a fixed percentage of the radius of the cornea 10. The percentage may be in the range of approximately 5 to 20 percent, such as for example, approximately 10 percent.

Figure 4B:
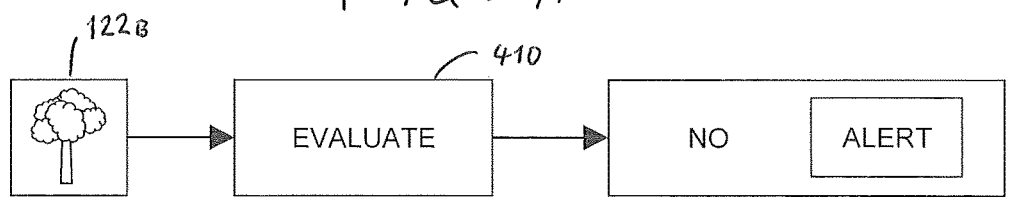

FIGS. 4A and 4B illustrate an example of the method 100 further comprising block 410 at which an evaluation as to whether or not the detected one or more objects 122 and/or (though not illustrated) activities 912 merit an alert 132 is made. The provision of the alert 132 (as per block 130) is conditional on this evaluation.

FIG. 4A illustrates an example in which an alert 132 is provided to the user for alerting the user to a detection of a first one or more objects $122_A$. FIG. 4B illustrates an example in which no alert is provided to the user for alerting the user to a detection of a second, different one or more objects $122_B$. In the case of the first one or more objects $122_A$, the evaluation determined that the alert 132 was merited whereas in the case of the second one or more objects $122_B$, the evaluation determined that the alert 132 was not merited.

Likewise, in some examples an alert 132 is provided to the user for alerting the user to the detection of a first one or more activities 912 while no alert is provided for alerting the user to the detection of a second, different one or more activities 912.

FIGS. 5 to 9 illustrate examples of the evaluation of block 410. FIGS. 5 to 7 illustrate examples in which the evaluation of block 410 is concerned with determining whether or not the user is already aware of the detected one or more objects 122 and/or activities 912. FIGS. 8 and 9 illustrate examples in which the evaluation of block 410 is concerned with the properties of the one or more objects 122 and/or activities 912 detected.

FIG. 5 illustrates an example of the method 100 further comprising an evaluation 410 for determining whether the user may have a persisting awareness of the one or more objects 122 and/or activities 912 detected.

In this example, an image $112_{t1}$ captured at a first time is processed as per block 120 of the method 100 to detect the one or more objects $122_{P\_t1}$ reflected by the peripheral portion 14 of the cornea 10 (for example, a car). One or more objects $122_{C\_t1}$ reflected by the central portion 12 of the cornea 10 are also detected (for example, a house). These one or more objects $122_{C\_t1}$ reflected by the central portion 12 of the cornea 10 are recorded in a record 510. The recording of the one or more objects $122_{C\_t1}$ reflected by the central portion 12 of the cornea 10 may comprise temporary recording and/or permanent recording.

An image $112_{t2}$ captured at a later time is processed as per block 120 of the method 100 to detect the one or more objects $122_{P\_t2}$ reflected by the peripheral portion 14 of the cornea 10 (for example, a house). These one or more objects $122_{P\_t2}$ reflected by the peripheral portion 14 of the cornea 10 are provided as an input to block 410 of the method 100 for evaluation. The evaluation comprises determining whether the one or more objects $122_{P\_t2}$ reflected by the peripheral portion 14 of the cornea 10 correspond to any objects reflected by the central portion 12 of the cornea 10 during a preceding period of time such as, for example, the one or more objects $122_{C\_t1}$.

These objects reflected by the central portion 12 of the cornea 10 during a preceding period of time can be retrieved from the record 510. In some examples the objects are recorded in the record 510 in association with a time that the image from which they were detected was captured. This enables the record 510 to be queried for objects detected during the preceding time period. In other examples, entries in the record 510 are only maintained for a time interval equal in duration to that of the preceding time period to which the detected one or more objects $122_{P\_t2}$ are compared.

The provision of the alert 132 (as per block 130) is conditional on the output of block 410. If the one or more objects $122_{P\_t2}$ reflected by the peripheral portion 14 of the cornea 10 correspond to any objects reflected by the central portion 12 of the cornea 10 during the preceding period of time (as is shown in the example of FIG. 6 where the house previously reflected by the central portion 12 of the cornea 10 is now reflected in the peripheral portion 14), no alert is provided to the user for alerting the user to the detection of the one or more objects $122_{P\_t2}$.

Those one or more objects $122_{P\_t2}$ reflected by the peripheral portion 14 of the cornea 10 which do not correspond to any objects reflected by the central portion 12 of the cornea 10 during the preceding period of time can be presumed to be objects of which the user is not aware. The alert 132 may then be provided for alerting the user to their detection or they may be fed forward in the method 100 for further evaluation.

Activities 912 detected based on one or more reflections by the peripheral portion 14 of the cornea 10 may also be compared with recorded activities which were previously detected based on one or more reflections by the central portion 12 of the cornea 10 for the purpose of determining whether the user has a persisting awareness of the activities 912 and thus whether no alert is required.

FIG. 6 illustrates an example of the method 100 further comprising an evaluation 410 for determining whether the user may be interacting with the one or more objects 112 and/or activities 912 other than by looking at them.

At block 610, the method 100, in this example, comprises determining whether the user is interacting with the one or more objects 122.

Determining whether the user is interacting with the one or more objects 122 can comprise processing the at least one image 122 to detect whether the user is in physical contact with the one or more objects 122. This can involve determining that one of the detected objects 122 is a human body part, such as a hand or digit, which:

extends, itself or via other body parts such as an arm, to the edge of the at least one image 112 (thus indicating that it is connected to and belongs to the user); and
 representation in the image adjoins or overlays a representation of another detected object 122 in the at least one image 112.

Where depth information is not available, a comparison between the scale of the representation of the body part and the scale of the representation of the another detected object 122 can be made and the detection of physical contact conditional on this comparison.

Alternatively, determining whether the user is interacting with the one or more objects 122 can comprise obtaining voice data of the user and processing the voice data to determine whether speech of the user is related to the detected one or more objects 122. For example, if the user mentions the detected one or more objects 122 in conversation or provides a voice command of an appropriate nature for the detected one or more objects 122 (including, for example, a command for a dog or other living creature), it can be presumed that the user is aware of these detected one or more objects 122.

At block 620, the method 100, in this example, comprises selecting those detected one or more objects 122 with which the user is not determined to be interacting. The alert 132 may then be provided for alerting the user to their detection or they may be fed forward in the method 100 for further evaluation.

If the user is determined to be interacting with the one or more objects 122, no alert is provided to the user for alerting the user to the detection of these objects.

In some examples, the objects with which the user is determined to interact in block 610 are recorded in the record 510 described in relation to FIG. 5 above. One or more objects $122_{P\_t2}$ subsequently reflected by the peripheral portion 14 of the cornea 10 can then be compared to objects retrieved from the record 510 to determine whether the one or more objects $122_{P\_t2}$ correspond to an object with which the user was determined to interact during the preceding period of time and/or which was reflected in the central portion 12 of the cornea 10 during the preceding period of time. If so, no alert is provided to the user for alerting the user to the detection of the one or more objects $122_{P\_t2}$.

FIG. 7 illustrates an example of the method 100 further comprising an evaluation 410 for determining whether the detected one or more objects 112 and/or activities 912 are in the user's immediate surroundings. More specifically, the evaluation 410 is for determining whether a proximity d of the one or more objects 122 to the user is within a threshold proximity Th.

In this example, the method 100 comprises obtaining at least one image of a left cornea of the user (hereinafter the at least one left image $112_L$) and at least one image of a right cornea of the user (hereinafter the at least one right image $112_R$). It is to be appreciated that the at least one left and right images $112_L$, $112_R$ may be obtained by means of capturing respective images or by capturing at least one image of both the left and right corneas.

Objects 122 and their respective positions ($r_L$, $\theta_L$) in the at least one left image $112_L$ and their respective positions ($r_R$, $\theta_R$) in the at least one right image $112_R$ can be obtained via image processing (as per method block 120).

At block 710, the method 100, in this example, comprises determining a proximity d of the one or more objects 122 to the user. In this example the proximity d is determined based on a parallax α of the one or more objects 122 between the at least one left image $112_L$ and at least one right image $112_R$. The angle between the one or more objects 122 and the view direction of each eye can be determined from the position of the one or more objects 122 in the images $112_L$, $112_R$. The distance between the two corneas can be known or measured from an image of both corneas. Thus, the distances of the one or more objects 122 from each cornea can be determined using the sine rule. The proximity d of the object 122 can be taken as the average of these distances.

In other examples the proximity d of the one or more objects 122 may be determined by considering a scale of the representations of the one or more objects 122 within the at least one image 112 (as compared to the real-world size of such objects 122). In still other examples additional depth data may be received from a sensor(s) configured for range imaging and the proximity d is based on this depth data.

At block 720, the method 100, in this example, comprises a comparison of the proximity d with a threshold proximity Th. If the one or more objects 122 are within the threshold proximity Th, no alert is provided to the user for alerting the user to the detection of the one or more objects 122.

The threshold proximity Th defines a region such that the user may be expected to have awareness of objects 122 or activities 912 within this region. This region may correspond to a user's personal space. The threshold proximity Th may be around 0.7 to 1.2 metres.

Those one or more objects 122 which are not within the threshold proximity Th can be presumed to be objects of which the user is not aware. The alert 132 may then be provided for alerting the user to their detection or they may be fed forward in the method 100 for further evaluation.

FIG. 8 illustrates an example of the method 100 further comprising an evaluation 410 for determining whether the detected one or more objects 122 have properties in respect of which the alert 132 is merited. Thus, in this example the provision of the alert 132 to the user for alerting the user to the detection of the one or more objects 122 (as per block 130) is conditional on one or more properties of the one or more objects 122.

At block 810, the method 100, in this example, comprises determining whether the one or more objects 122 have properties which match target properties 812. If so, the alert 132 is provided for alerting the user to their detection (as per block 130) or they may be fed forward in the method 100 for further evaluation. If not, no alert is provided or the provision of the alert 132 may be conditional upon detection of an activity 912 involving the one or more objects 122 which is determined to be of interest to the user as described in relation to FIG. 9 below.

The target properties 812 can relate to, for example: an identity of an object; a location of an object relative to the user; and/or a movement of an object.

The target properties 812 in relation to the identity of an object can comprise one or more identities of objects which are likely to be of interest to the user.

The target properties 812 can comprise identities of objects of general interest to multiple users such as, for example, hazardous objects or objects associated with a hazard or local attractions or interest points.

The target properties 812 can also be personalized for the user and comprise identities of objects which are of personal interest to the user.

For example, the target properties 812 can comprise the identities of people associated with the user such as their children, spouse, friends etc. The identities of these people can be represented by a set of faces and the detected one or more objects 122 can be compared with this set of faces to determine whether there is a match indicative of the presence of respective people in the user's environment.

These target properties 812 can be retrieved from a database containing, for example, user preferences, interests, images of people known to the user, social network data etc.

Target properties 812 which are personalized for the user can be specified by the user or can be learnt based on the user's response to particular objects. The user's response can be determined by, for example, sensing one or more actions (such as body movements or facial expressions) performed by the user in a time period following interaction with or relating to those particular objects or by physiological sensing (such as heart rate, breathing rate, or body temperature monitoring) in a time period following interaction with or relating to those particular objects.

The target properties 812 in relation to the location of an object relative to the user can comprise a proximity of the object to the user. While a first threshold Th in relation to proximity has been described above in relation to FIG. 7, additionally or alternatively there can be defined a second threshold proximity where objects which are not within this second threshold proximity are not considered to be of immediate interest to the user. That is, objects which are sufficiently far away from the user may not be considered to be of interest to the user. This second threshold proximity may vary for different identities of the objects. It should be noted that this second threshold proximity is different to the first threshold proximity Th described in relation to FIG. 7.

The target properties 812 in relation to the location of an object relative to the user can additionally or alternatively comprise a part of the user's visual field in which the object may appear.

The target properties 812 in relation to the movement of an object can comprise a nature of the movement, for example approaching the user versus periodic motion about a location displaced from the user. For example, objects approaching the user may be considered to be of greater interest to the user. The target properties 812 in relation to the movement of an object can additionally or alternatively comprise a speed of the object. For example, objects moving at speeds above a threshold may be considered to be of greater interest to the user.

The properties of the one or more objects 122 can be determined by processing the at least one image 112 of the cornea 10, by processing a plurality of images 112 of the cornea 10 at different times, and/or based on additional data obtained by other sensors 1514 (see FIG. 15).

Identities of the one or more objects 122 can be determined as part of the detection of block 210.

The identities can be corroborated by data received from other sensors 1514 such as one or more microphones or other means for obtaining audio data. The audio data can be processed to detect sounds associated with the identities of the one or more objects 122. For example, if the detection of block 210 returns the identity of an object as a car (that is, the detection of block 210 determines that a car is reflected by the cornea 10 of the user), audio data can be processed to determine whether sounds characteristic of a car can be discerned. In some examples, multiple microphones can be used in order to locate the sound source and the corroboration can involve checking whether or not the one or more objects 122 and the sound sources have substantially the same location.

Locations of the one or more objects 122 can be determined from a position of representations of the one or more objects 122 in the at least one image 112. The positions can be returned with the identity of the one or more objects 122 as an output of the detection of block 210. Optionally a depth component of the location of the one or more objects 122 can also be determined based on: parallax $\alpha$ as described in relation to FIG. 7 above; a scale of the representations of the one or more objects 122 within the at least one image 112; or additional depth data received from a sensor(s) configured for range imaging.

Locations of the one or more objects 122 can also be determined using multiple microphones to locate a source of sounds which are characteristic of the one or more objects 122 detected.

Movements of the one or more objects 122 can be determined by tracking the one or more objects 122 over a plurality of images 112 captured at different times.

Movements of the one or more objects 122 can also be determined based on data from other sensors 1514 such as one or more microphones or other means for obtaining audio data. The audio data can be processed to detect sounds associated with movements of the one or more objects 122. For example, if the detection of block 210 returns the identity of an object as a car (that is, the detection of block 210 determines that a car is reflected by the cornea 10 of the user), audio data can be processed to determine whether sounds characteristic of a car being driven can be discerned. If so, it can be determined that the detected car is being driven. If not, it can be determined that the car is stationary.

FIG. 9 illustrates an example of the method 100 further comprising an evaluation 410 of the one or more activities 912 detected based on reflections by the cornea 10 of the user.

In this example a plurality of images $112_{t1}$, $112_{t2}$, $112_{t3}$, . . . , $112_{tN}$ of the cornea 10 of the user are captured at different times. These plurality of different images $112_{t1}$, $112_{t2}$, $112_{t3}$, . . . $112_{tN}$ may be frames of a captured video of the cornea 10 of the user.

At block 910, the method 100, in this example, comprises activity detection. The activity detection can comprise vision-based activity detection. The activity detection can comprise determining one or more activities 912 based on changes concerning the one or more objects 122 between the plurality of images $112_{t1}$, $112_{t2}$, $112_{t3}$, . . . $112_{tN}$. For example, the activity detection can be based on a two-stream convolutional network approach in which a spatial stream to detect the one or more objects 122 is implemented by a deep convolutional network and a temporal stream to detect movement of the one or more objects 122 across the plurality of images $112_{t1}$, $112_{t2}$, $112_{t3}$, . . . $112_{tN}$ is implemented by a different deep convolutional network. Softmax scores of each deep convolutional network are combined by late fusion. An example of a two-stream convolutional network approach is described in Simonyan, K., & Zisserman, A. (2014). Two-stream convolutional networks for action recognition in videos. In *Advances in neural information processing systems* (pp. 568-576).

In other examples, activity detection to determine one or more activities 912 can be based on extraction of spatiotemporal features from the plurality of images $112_{t1}$, $112_{t2}$, $112_{t3}$, . . . $112_{tN}$ without separately detecting one or more objects 122 in each of the images. That is, rather than detecting one or more objects 122 and determining one or more activities 912 based on changes concerning the one or more objects 122 between the plurality of images $112_{t1}$, $112_{t2}$, $112_{t3}$, . . . $112_{tN}$, the method 100 can comprise processing the plurality of images $112_{t1}$, $112_{t2}$, $112_{t3}$, . . . $112_{tN}$ to detect one or more activities 912 based on reflections by the cornea 10 of the user.

At block 920, the method 100, in this example, comprises determining whether the one or more activities 912 match target activities 922. If so, the alert 132 is provided to the user as per block 130 of the method 100 or the one or more activities 912 may be fed forward in the method 100 for further evaluation. If not, no alert is provided to the user in respect of the detection of the one or more activities 912.

The target activities 922 can comprise identities of activities which are likely to be of interest to the user.

The target activities 922 can comprise identities of activities of general interest to multiple users such as, for example, activities which may pose a threat to the user's safety such as a skidding or otherwise out-of-control vehicle.

The target activities 922 can also be personalized for the user and comprise identities of activities which are of personal interest to the user. For example, the target activities 922 can comprise a football match if the user is known to be interested in football or a passing bird if the user is known to be interested in bird watching.

Target activities 922 which are personalized for the user can be specified by the user or can be learnt based on the user's response to particular activities. The user's response can be determined by, for example, sensing one or more actions (such as body movements or facial expressions) performed by the user in a time period beginning with engagement in or observation of those particular activities or by physiological sensing (such as heart rate, breathing rate, or body temperature monitoring) in a time period beginning with engagement in or observation of those particular activities.

In some examples, the provision of the alert 132 to the user for alerting the user to the detection of the one or more objects 122 is conditional on an identity of the one or more activities 912 determined in respect of the one or more objects 122.

In other examples, where the provision of the alert 132 to the user is for alerting the user to the detection of the one or more activities 912, the provision of the alert 132 is conditional on an identity of the one or more activities 912.

By alerting the user to the detection of objects (as per the example of FIG. 8) or activities (as per the example of FIG. 9) which are likely to be of interest to the user, the user can be prompted to reduce time attending to tasks at an apparatus for performing the method 100. Excessive time spent attending to tasks at the apparatus can have a detrimental effect on the mental well-being of the user, a direct detrimental effect on the physical well-being of the user such as eye strain or repetitive strain injury (RSI), and a detrimental effect on the power consumption of the apparatus. The alert 132 can therefore ameliorate the aforementioned detrimental effects.

The method 100 can comprise one or more of the evaluations 410 described in relation to FIGS. 5 to 9 above. Where the method 100 comprises multiple evaluations 410, these may be performed in series, one after the other. There may be no particular order in which these evaluations 410 should be performed. Therefore, these evaluations 410 may also be performed in parallel. Performing these evaluations 410 in series can save computing resources as compared to performing them in parallel because detected objects 122 which do not meet the criteria of one evaluation may not be passed on to the next evaluation. Performing these evaluations 410 in parallel can save time as compared to performing them in series, enabling the alert 132 to be provided closer to real-time.

In some examples, the distinction made between objects $122_C$ reflected by the central portion 12 of the cornea 10 and objects $122_P$ reflected by the peripheral portion 14 of the cornea 10 as described above in relation to FIG. 2 can also be performed as part of the series or parallel evaluations 410. In such example, however, the distinction made between objects $122_C$ and objects $122_P$ is at least a precursor to the evaluation 410 described in relation to FIG. 5, thus these would be performed in series, even if in parallel with the rest.

FIG. 10 illustrates an example of the alert 132. In this example the alert 132 is in the form of a visual output.

The output of a display is illustrated. Frames 1 to N ($F_1$, $F_2$, ... $F_N$) of visual content 1001 are displayed to the user. The capturing of and the processing of the at least one image 112 (as per blocks 110 and 120 respectively) are at least substantially transparent to the user. The visual content 1001 is displayed to the user while the at least one image 112 is captured and processed and may be related to a task to which the user is attending.

As illustrated, the alert 132 comprises a temporary interrupt to the displayed visual content 1001. In this example, the temporary interruption causes the display of successive frames $F_1$ to $F_N$ of the visual content 1001 to be paused for the duration of the alert 132. Subsequently the display of the visual content 1001 is resumed with the frame $F_7$ which follows the last frame $F_6$ to be displayed according to the sequence of frames in the visual content 1001.

In other examples, the alert 132 may comprise a modification of a frame of the visual content 1001. For example, rather than delaying frame $F_7$ as in the illustrated example, the alert 132 may modify frame $F_7$. Should the alert 132 have a longer duration than frame $F_7$, then the alert may modify subsequent frames too. The modification may comprise an overlay of visual content for alerting the user to the detection of the one or more objects 122 and/or activities 912.

In still other examples, the alert 132 replaces frames of the visual content 1001 for the duration of the alert 132. For example, rather than delaying the display of frame $F_7$, frame $F_7$ is never displayed and is replaced by the alert 132, the display of the visual content 1001 resuming after the alert 132 with a later frame. That is, the alert 132 is provided to the user while a task to which the user was attending continues to execute but with no visual output 1001 for the duration of the alert 132.

Although the visual content 1001 is illustrated as comprising a sequence of frames, it is to be appreciated that the visual content 1001 may remain static and the alert 132 may interrupt or modify the display of that static visual content 1001 temporarily before display of the static visual content 1001 is resumed.

In some examples, the temporary interrupt comprises displaying a visual representation of the one or more objects 122 and/or activities 912 to the user. The visual representation may not comprise the whole of the at least one image 112 of the cornea 10 of the user. In some examples, the visual representation may not even comprise a part of the at least one image 112. Instead, the visual representation of the one or more objects 122 and/or activities 912 may comprise a schematic illustration of the one or more objects 122 and/or activities 912 or of objects and/or activities of the same identity or class as the one or more objects 122 and/or activities 912 detected.

The visual representations may comprise blurred shapes of the one or more objects 112 or avatars of people detected.

By displaying a visual representation of the one or more objects 122 and/or activities 912 to the user at an apparatus at which the user is attending a task, the one or more objects 122 and/or activities 912 are effectively moved from the user's peripheral vision into the user's central vision, thus increasing the likelihood of the user gaining awareness of the one or more objects 122 and/or activities 912.

In some examples, the alert 132 is configured to indicate a location of the one or more objects 122 and/or activities 912 relative to the user. For example, the alert 132 can comprise an arrow rendered on the display and pointing in the direction of the location of the one or more objects 122 and/or activities 912. Additionally or alternatively, the aforementioned representation of the one or more objects 122 and/or activities 912 can be rendered on the display with a displacement from the centre of the display which corresponds to the direction of the location of the one or more objects 122 and/or activities 912.

The indication of the location of the one or more objects 122 and/or activities 912 can change as the location of the one or more objects 122 and/or activities 912 changes relative to the user. The change of the indication may be in real-time and synchronized with the change in location of the one or more objects 122 and/or activities 912.

Where the alert 132 is a non-visual output, the alert 132 may still be configured to indicate a location of the one or more objects 122 and/or activities 912 relative to the user. For example, spatial audio can be used to provide the alert 132 as a sound source at or in the direction of the location of the one or more objects 122 and/or activities 912. "Spatial audio" is the rendering of a sound scene. "Sound scene" refers to a representation of the sound space listened to from a particular point-of-view (position) within the sound space. "Sound space" refers to an arrangement of sound sources in a three-dimensional space.

FIG. 11 illustrates an example of an additional condition for providing the alert 132 (as per block 130). In this example of the method 100, the provision of the alert 132 is conditional on a determination that the user is looking at the apparatus for performing the method 100 when the at least one image 112 is captured. For example, the alert 132 may be provided to the user when the user is attending to a task at the apparatus but not when the user is not attending to a task at the apparatus.

At block 1110, the method 100, in this example, comprises processing the at least one image 112 to detect whether the apparatus is reflected by the central portion 12 of the cornea 10. For example, if an object 122$_C$ reflected by a central portion 12 of the cornea 10 matches a representation 1112 of how the apparatus (or visual content 1001 displayed at the apparatus) would appear as reflected by the central portion 12 of the cornea 10, then it is determined that the apparatus is reflected by the central portion 12 of the cornea 10. If the apparatus is reflected by a central portion 12 of the cornea 10, then it is determined that the user was looking at the apparatus when the at least one image 112 was captured.

In other examples, other gaze tracking systems, such as electrooculography (EOG), can be used to determine where the user is looking, and thus whether the user is looking at the apparatus for performing the method 100 when the at least one image 112 is captured.

In other examples, it can be determined whether the user is attending to a task at the apparatus when the at least one image 112 is captured by correlating electroencephalography (EEG) signals to changes and features of the displayed visual content 1001. For example, a steady state flicker can be introduced to a feature of the visual content 1001 which can be detected from EEG signals when the user is looking at it. This steady state flicker can be made imperceptible or barely perceptible consciously.

FIG. 12 illustrates an example of the method 100 which further comprises performing image corrections on the at least one image 112 of the cornea 10 of the user before detecting the one or more objects 122 and/or activities 912 (as per block 210). The corrected at least one image is denoted by 112' in FIG. 12.

At block 1210, the method 100, in this example, comprises one or more of the following image corrections:
  applying a transformation, based on a geometric model of the cornea 10, to the at least one image 112, wherein the transformation may correct for the distortions introduced by the cornea 10 acting as a convex mirror;
  determining a point spread function based on a comparison of displayed visual content 1001 as reflected by the cornea 10 of the user with the visual content 1001 as displayed, and performing a deconvolution, based on the point spread function, of the at least one image 112, wherein the deconvolution may remove blur from the at least one image 112;
  recognising invariant features, such as the iris 30 and pupil 40, in the at least one image 112 and filtering out these invariant features using one or more AI algorithms; or
  detecting duplicate features in the at least one image 112, classifying the duplicate features as reflections by the cornea 10 or reflections by the iris 30 based on differing spatial warping and spectral signature, and filtering out those features which are reflections by the iris 30.

FIG. 13 illustrates an example of a controller 1310. Implementation of a controller 1310 may be as controller circuitry. The controller 1310 may be implemented in hardware alone, have certain aspects in software including firmware alone or can be a combination of hardware and software (including firmware).

As illustrated in FIG. 13 the controller 1310 may be implemented using instructions that enable hardware functionality, for example, by using executable instructions of a computer program 1316 in a general-purpose or special-purpose processor 1312 that may be stored on a computer readable storage medium (disk, memory, etc.) to be executed by such a processor 1312.

The processor 1312 is configured to read from and write to the memory 1314. The processor 1312 may also comprise an output interface via which data and/or commands are output by the processor 1312 and an input interface via which data and/or commands are input to the processor 1312.

The memory 1314 stores a computer program 1316 comprising computer program instructions (computer program code) that controls the operation of the apparatus 1510 when loaded into the processor 1312. The computer program instructions, of the computer program 1316, provide the logic and routines that enables the apparatus to perform the methods illustrated in FIGS. 1A to 12. The processor 1312 by reading the memory 1314 is able to load and execute the computer program 1316.

The apparatus 1510 therefore comprises:
  at least one processor 1312; and
  at least one memory 1314 including computer program code
  the at least one memory 1314 and the computer program code configured to, with the at least one processor 1312, cause the apparatus 1510 at least to perform:
    capturing at least one image 112 of a cornea 10 of the user;
    processing the at least one image 112 to detect one or more objects 122 and/or activities 912 based on one or more reflections by a peripheral portion 14 of the cornea 10; and
    providing an alert 132 to the user for alerting the user to the detection of the one or more objects 122 and/or activities 912.

As illustrated in FIG. 14, the computer program 1316 may arrive at the apparatus 1510 via any suitable delivery mechanism 1410. The delivery mechanism 1410 may be, for example, a machine readable medium, a computer-readable medium, a non-transitory computer-readable storage medium, a computer program product, a memory device, a record medium such as a Compact Disc Read-Only Memory (CD-ROM) or a Digital Versatile Disc (DVD) or a solid state memory, an article of manufacture that comprises or tangibly embodies the computer program 1316. The delivery mechanism may be a signal configured to reliably transfer the computer program 1316. The apparatus 1510 may propagate or transmit the computer program 1316 as a computer data signal.

Computer program instructions for causing an apparatus to perform at least the following or for performing at least the following:
  causing at least one image 112 of a cornea 10 of the user to be captured;
  processing the at least one image 112 to detect one or more objects 122 and/or activities 912 based on one or more reflections by a peripheral portion 14 of the cornea 10; and
  causing an alert 132 to be provided to the user for alerting the user to the detection of the one or more objects 122 and/or activities 912.

The computer program instructions may be comprised in a computer program, a non-transitory computer readable medium, a computer program product, a machine readable medium. In some but not necessarily all examples, the computer program instructions may be distributed over more than one computer program.

Although the memory 1314 is illustrated as a single component/circuitry it may be implemented as one or more separate components/circuitry some or all of which may be integrated/removable and/or may provide permanent/semi-permanent/dynamic/cached storage.

Although the processor 1312 is illustrated as a single component/circuitry it may be implemented as one or more separate components/circuitry some or all of which may be integrated/removable. The processor 1312 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' may refer to one or more or all of the following:
(a) hardware-only circuitry implementations (such as implementations in only analog and/or digital circuitry) and
(b) combinations of hardware circuits and software, such as (as applicable):
(i) a combination of analog and/or digital hardware circuit(s) with software/firmware and
(ii) any portions of hardware processor(s) with software (including digital signal processor(s)), software, and memory(ies) that work together to cause an apparatus, such as a mobile phone or server, to perform various functions and
(c) hardware circuit(s) and or processor(s), such as a microprocessor(s) or a portion of a microprocessor(s), that requires software (e.g. firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor and its (or their) accompanying software and/or firmware. The term circuitry also covers, for example and if applicable to the particular claim element, a baseband integrated circuit for a mobile device or a similar integrated circuit in a server, a cellular network device, or other computing or network device.

The blocks illustrated in the FIGS. 1A to 12 may represent steps in a method and/or sections of code in the computer program 1316. The illustration of a particular order to the blocks does not necessarily imply that there is a required or preferred order for the blocks and the order and arrangement of the block may be varied. Furthermore, it may be possible for some blocks to be omitted.

FIG. 15 illustrates an example of an apparatus 1510 for preforming the method 100 as described in relation to FIGS. 1A to 12. The apparatus 1510 may be or may comprise the controller 1310 of FIG. 13 or may be or may comprise any computer or machine capable of reading the computer program 1316 from the delivery mechanism 1410 of FIG. 14 and running that computer program 1316.

In this example the apparatus 1510 further comprises the camera 20 of FIG. 1B. The camera 20 is configured to capture at least one image 112 or a video of the cornea 10 of the user.

The camera 20 may capture the at least one image 112 or video while the user is attending to a task via interaction with a display. Therefore, the camera 20 can be disposed proximate the display and configured to receive light from a field of view in front of the display. For example, the camera 20 may be a front-facing camera of a personal computer. Therefore, even if the personal computer is held or positioned in a way that a rear-facing camera of the personal computer does not view the environment in front of the user, this environment can still be imaged by the front-facing camera 20 by means of the reflections by the cornea 10 of the user.

The camera 20 can, in some examples, also be used to sense the response of the user to objects or activities to enable learning of objects and/or activities which are of personal interest to the user, as described in relation to FIGS. 8 and 9 above. For example, the camera 20 can be utilized for capturing image data from which actions or physiological parameters can be sensed. For example, body movement and facial expressions can be sensed from image data. Likewise, for example, breathing rate and body temperature (by means of skin color changes) can be sensed from image data.

In this example the apparatus 1510 further comprises one or more user interfaces (UIs) 1512. The one or more UIs 1512 are configured to provide the alert 132 and, in some examples, to display the visual content 1001 to the user.

The one or more UIs 1512 can comprise a display for displaying the visual content 1001 and/or for providing the alert 132 in the form of a visual output. The camera 20 can be disposed proximate this display and configured to receive light from a field of view in front of this display.

The one or more UIs 1512 can comprise a haptic device or actuators configured to provide haptic output to the user for example when the alert 132 comprises a haptic output.

The one or more UIs 1512 can comprise a speaker configured to provide audio output to the user for example when the alert 132 comprises an audio output.

The provision of the alert 132 as a sound source at or in the direction of the location of the one or more objects 122 and/or activities 912 can be performed by, without limitation: headphone speakers connected (wired or wirelessly) to the apparatus 1510 and using head-related transfer functions (HRTF) to synthesize binaural sound; by one or more networked speakers at locations external to the apparatus 1510; or a parametric speaker comprised in the apparatus 1510.

The one or more networked speakers at locations external to the apparatus 1510 may comprise directional speaker such as a directional soundbar comprising an array of speakers or a parametric speaker.

A parametric speaker is a particular type of directional speaker which comprises an array of ultrasonic transducers. The use of high-frequencies, such as ultrasonic frequencies, reduces diffraction as compared to audible frequencies. Thus, an array of ultrasonic transducers can project a narrow beam in a desired direction. The array of ultrasonic transducers produces a narrow, modulated beam comprising a carrier signal and a modulating signal, both at ultrasonic frequencies. For example, the carrier signal may have a constant frequency of 200 kHz and the modulating signal may fluctuate within a frequency band between 200,200 Hz and 220 kHz. When the narrow, modulated beam collides with an obstacle, the carrier signal and modulating signal interfere to produce a third signal in the audible frequency band, for example 200 Hz to 20 kHz. To make sounds appear to come from a particular direction, the apparatus 1510 may cause the narrow, modulated beam to be directed at an obstacle lying in that particular direction to create an audible sound source at the location of that obstacle such that sounds appears to be coming from that particular direction.

In some, but not necessarily all, examples the apparatus 1510 further comprises one or more additional sensors 1514. The one or more additional sensors 1514 can be configured to obtain information about the detected one or more objects 122 and/or activities 912 such as about location and movement as described in relation to FIG. 8 above.

The one or more additional sensors 1514 can comprise one or more microphones to obtain audio data and/or one or more sensors configured for range imaging to obtain depth information Other sensors can include vibration sensors (such as microelectromechanical vibration sensors) and additional image sensors (such as a rear-facing camera) which can be used to obtain image information about portions of the user's environment obscured by the apparatus 1510 in the at least one image 112.

The one or more additional sensors 1514 can, in some examples, also be used to sense the response of the user to objects or activities to enable learning of objects and/or activities which are of personal interest to the user, as described in relation to FIGS. 8 and 9 above. For example, a microphone can be used to, for example, sense a breathing rate of the user. An infrared heat sensor can be used to measure a body temperature of the user. A wearable inertial measurement unit (IMU) can be used to detect facial expressions. The wearable IMU can be worn in or on the ear. The wearable IMU may be configured as an earbud and may comprise a speaker enabling audio outputs. The data from the IMU can be correlated with facial expressions either through a plurality of predetermined threshold values or through a model that has been trained, through machine learning, using training data comprising data from the IMU labelled with corresponding facial expressions. The training may be a supervised classification. Other wearable sensors can be used to measure physical physiological parameters or biochemical physiological parameters. These wearable sensors can be invasive or non-invasive. The use of such wearable sensors can enable, for example, pulse oximetry, blood pressure monitoring, and sweat monitoring.

In some examples the apparatus 1510 is an electronic device. The apparatus 1510 may be an electronic communications device such as a personal computer. The electronic device may be a portable electronic communications device such as a handheld electronic communications device or a wearable electronic communications device. The apparatus 1510 may be configured for mobile cellular communication. The apparatus 1510 may be a smartphone, a smartwatch, or another type of portable personal computer.

It is to be appreciated that the apparatus 1510 may comprise any suitable means for performing the functions hereinbefore described.

Consequently, in some examples, the apparatus 1510 comprises means for:
capturing at least one image 112 of a cornea 10 of the user;
processing the at least one image 112 to detect one or more objects 122 and/or activities 912
based on one or more reflections by a peripheral portion 14 of the cornea 10; and
providing an alert 132 to the user for alerting the user to the detection of the one or more objects 122 and/or activities 912.

Where a structural feature has been described, it may be replaced by means for performing one or more of the functions of the structural feature whether that function or those functions are explicitly or implicitly described.

The recording of data may comprise only temporary recording, or it may comprise permanent recording or it may comprise both temporary recording and permanent recording, Temporary recording implies the recording of data temporarily. This may, for example, occur during sensing or image capture, occur at a dynamic memory, occur at a buffer such as a circular buffer, a register, a cache or similar. Permanent recording implies that the data is in the form of an addressable data structure that is retrievable from an addressable memory space and can therefore be stored and retrieved until deleted or over-written, although long-term storage may or may not occur. The use of the term 'capture' in relation to an image relates to temporary recording of the data of the image. The use of the term 'store' in relation to an image relates to permanent recording of the data of the image.

The apparatus, methods and computer programs may use machine learning which can include statistical learning. Machine learning is a field of computer science that gives computers the ability to learn without being explicitly programmed. The computer learns from experience E with respect to some class of tasks T and performance measure P if its performance at tasks in T, as measured by P, improves with experience E. The computer can often learn from prior training data to make predictions on future data. Machine learning includes wholly or partially supervised learning and wholly or partially unsupervised learning. It may enable discrete outputs (for example classification, clustering) and continuous outputs (for example regression). Machine learning may for example be implemented using different approaches such as cost function minimization, artificial neural networks, support vector machines and Bayesian networks for example. Cost function minimization may, for example, be used in linear and polynomial regression and K-means clustering. Artificial neural networks, for example with one or more hidden layers, model complex relationship between input vectors and output vectors. Support vector machines may be used for supervised learning. A Bayesian network is a directed acyclic graph that represents the conditional independence of a number of random variables.

The above described examples find application as enabling components of:
automotive systems; telecommunication systems; electronic systems including consumer electronic products; distributed computing systems; media systems for generating or rendering media content including audio, visual and audio visual content and mixed, mediated, virtual and/or augmented reality; personal systems including personal health systems or personal fitness systems; navigation systems; user interfaces also known as human machine interfaces; networks including cellular, non-cellular, and optical networks; ad-hoc networks; the internet; the internet of things; virtualized networks; and related software and services.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although examples have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain examples, those features may also be present in other examples whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning then it will be made clear in the context. In some circumstances the use of 'at least one' or 'one or more' may be used to emphasis an inclusive meaning but the absence of these terms should not be taken to infer any exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus comprising:
   at least one processor; and
   at least one memory including computer program code,
   the at least one memory and the computer program code configured to, with the at least one processor, cause the apparatus at least to perform:
   capture at least one image of a cornea of the user;
   apply a transformation, based on a geometric model of the cornea, to the at least one image, wherein the transformation modifies the at least one image to perform at least one of reducing or removing one or more distortions introduced by the cornea of the user;
   detect one or more objects or activities in a user environment based on one or more reflections by a peripheral portion of the cornea captured in the at least one image; and
   provide an alert to the user for alerting the user to the detection of the one or more objects or activities.

2. The apparatus as claimed in claim 1 wherein detecting one or more objects or activities in the user environment based on one or more reflections by a peripheral portion of the cornea captured in the at least one image comprises:
   detecting one or more objects or activities based on one or more reflections by the cornea;
   determining which of the one or more objects or activities are represented in a portion of the at least one image corresponding to the peripheral portion of the cornea; and
   selecting those one or more objects or activities which are determined to be represented in the portion of the at least one image corresponding to a peripheral portion of the cornea.

3. The apparatus as claimed in claim 1 wherein the at least one memory and the computer program code are configured to, with the at least one processor, cause the apparatus at least to further perform: remove a portion of the at least one image corresponding to a central portion of the cornea before processing the at least one image to detect one or more objects or activities based on one or more reflections by the peripheral portion of the cornea.

4. The apparatus as claimed in claim 1 wherein the at least one memory and the computer program code are configured to, with the at least one processor, cause the apparatus at least to further perform:
   record objects or activities detected based on one or more reflections by a central portion of the cornea;
   determine whether the one or more objects or activities detected based on one or more reflections by the peripheral portion of the cornea correspond to an object or activity detected based on one or more reflections by the central portion of the cornea during a preceding period of time; and
   if the one or more objects or activities detected based on one or more reflections by the peripheral portion of the cornea correspond to an object or activity detected based on one or more reflections by the central portion of the cornea during the preceding period of time, no alert is provided to the user for alerting the user to the detection of the one or more objects or activities.

5. The apparatus as claimed in claim 1 wherein the at least one memory and the computer program code are configured to, with the at least one processor, cause the apparatus at least to further perform:

determine whether the user is interacting with the one or more objects; and if the user is determined to be interacting with the one or more objects, no alert is provided to the user for alerting the user to the detection of the one or more objects.

6. The apparatus as claimed in claim 1 wherein the at least one memory and the computer program code are configured to, with the at least one processor, cause the apparatus at least to further perform: obtain at least one image of a left cornea of the user and at least one image of a right cornea of the user;

determine a proximity of the one or more objects to the user based on a parallax of the one or more objects between the at least one image of a left cornea of the user and at least one image of a right cornea of the user; and if the one or more objects are within a threshold proximity, no alert is provided to the user for alerting the user to the detection of the one or more objects.

7. The apparatus as claimed in claim 1 wherein the provision of the alert to the user for alerting the user to the detection of the one or more objects is conditional on one or more properties of the one or more objects, wherein the one or more properties comprise one or more of: an identity of the one or more objects; a location of the one or more objects relative to the user; a movement of the one or more objects.

8. The apparatus as claimed in claim 1 wherein the at least one memory and the computer program code are configured to, with the at least one processor, cause the apparatus at least to further perform: capture a plurality of images of the cornea of the user at different times; and determine one or more activities based on changes concerning the one or more objects between the plurality of images, wherein the provision of the alert to the user for alerting the user to the detection of the one or more objects or activities is conditional on an identity of the determined one or more activities.

9. The apparatus as claimed in claim 1 wherein the alert comprises a visual output.

10. The apparatus as claimed in claim 1 wherein the at least one memory and the computer program code are configured to, with the at least one processor, cause the apparatus at least to further perform: display visual content while capturing and processing the at least one image, and wherein the alert comprises a temporary interrupt to the displayed visual content.

11. The apparatus as claimed claim 10 wherein the temporary interrupt comprises displaying a visual representation of the one or more objects or activities to the user.

12. The apparatus as claimed in claim 1 wherein the alert comprises a haptic output or an auditory output.

13. The apparatus as claimed in claim 1 wherein the alert is configured to indicate a location of the one or more objects or activities relative to the user.

14. The apparatus as claimed in claim 1 wherein the provision of the alert is conditional on a determination that the user is looking at the apparatus when the at least one image is captured.

15. The apparatus as claimed in claim 1 wherein the at least one image comprises the one or more reflections by the cornea.

16. The apparatus as claimed in claim 1 wherein the one or more reflections comprise one or more reflections of the one or more objects or activities.

17. A method comprising:

capture at least one image of a cornea of the user;

apply a transformation, based on a geometric model of the cornea, to the at least one image, wherein the transformation modifies the at least one image to perform at least one of reducing or removing one or more distortions introduced by the cornea of the user;

detect one or more objects or activities in a user environment based on one or more reflections by a peripheral portion of the cornea captured in the at least one image; and provide an alert to the user for alerting the user to the detection of the one or more objects or activities.

18. The method as claimed in claim 17 wherein the at least one image comprises the one or more reflections by the cornea, and wherein the one or more reflections comprise one or more reflections of the one or more objects or activities.

19. A non-transitory computer readable medium comprising program instructions stored thereon for performing at least the following:

cause at least one image of a cornea of the user to be captured;

apply a transformation, based on a geometric model of the cornea, to the at least one image, wherein the transformation modifies the at least one image to perform at least one of reducing or removing one or more distortions introduced by the cornea of the user;

detect one or more objects or activities in a user environment based on one or more reflections by a peripheral portion of the cornea captured in the at least one image; and cause an alert to be provided to the user for alerting the user to the detection of the one or more objects or activities.

20. The non-transitory computer readable medium of claim 19, wherein the at least one image comprises the one or more reflections by the cornea, and wherein the one or more reflections comprise one or more reflections of the one or more objects or activities.

* * * * *

UNITED STATES PATENT AND TRADEMARK OFFICE
CERTIFICATE OF CORRECTION

| | |
|---|---|
| PATENT NO. | : 11,328,508 B2 |
| APPLICATION NO. | : 17/030224 |
| DATED | : May 10, 2022 |
| INVENTOR(S) | : Christopher Wright et al. |

It is certified that error appears in the above-identified patent and that said Letters Patent is hereby corrected as shown below:

In the Claims

In Column 23, Claim 11, Line 50, delete "claimed claim" and insert -- claimed in claim --, therefor.

Signed and Sealed this
Twenty-third Day of May, 2023

Katherine Kelly Vidal
*Director of the United States Patent and Trademark Office*